United States Patent [19]

Toikka

[11] Patent Number: 5,574,151
[45] Date of Patent: Nov. 12, 1996

[54] PROCESS FOR THE PREPARATION OF SENNOSIDES A AND B

[75] Inventor: Jarmo Toikka, Turku, Finland

[73] Assignee: Leiras Oy, Turku, Finland

[21] Appl. No.: 357,443

[22] Filed: Dec. 16, 1994

[30] Foreign Application Priority Data

Dec. 17, 1993 [FI] Finland .................................. 935715

[51] Int. Cl.$^6$ ............................. C07H 1/00; A61K 31/70
[52] U.S. Cl. ......................... 536/124; 536/4.1; 536/18.5; 536/127
[58] Field of Search .......................... 424/195.1; 536/124, 536/127, 128, 4.1, 18.5

[56] References Cited

U.S. PATENT DOCUMENTS

| | | | |
|---|---|---|---|
| 4,256,875 | 3/1981 | Gabriel et al. | 536/4.1 |
| 4,402,944 | 9/1983 | Callahan et al. | 514/33 |
| 4,511,561 | 4/1985 | Madaus et al. | 424/195.1 |
| 4,595,592 | 6/1986 | Hietala | 424/195.1 |
| 5,232,699 | 8/1993 | Colliopoulos | 424/195.1 |
| 5,391,775 | 2/1995 | Carcasona et al. | 552/262 |
| 5,393,898 | 2/1995 | Carcasona et al. | 552/262 |

FOREIGN PATENT DOCUMENTS 9300350  7/1993  WIPO.

OTHER PUBLICATIONS

*Progress in the Chemistry of Natural Products,* Stoll et al., Springer–Verlag, pp. 248–269, (1950).

*Primary Examiner*—John Kight
*Assistant Examiner*—Howard C. Lee

[57] ABSTRACT

The invention concerns a process for the preparation of sennosides A and B, wherein rheinanthrone-8-glucoside is oxidized with oxygen or an oxygen source to the sennosides A and B. According to the invention, the oxidation is carried out using active carbon as a catalyst, and, if desired, the obtained sennosides A and B are converted to their calcium salts using methanol precipitation from a calcium ion containing aqueous solution.

9 Claims, No Drawings

PROCESS FOR THE PREPARATION OF SENNOSIDES A AND B

BACKGROUND OF THE INVENTION

The object of the present invention is a process for the preparation of sennosides A and B, wherein rheinanthrone-8-glucoside is oxidized with oxygen or an oxygen source to form sennosides A and B.

The sennosides are agents with laxative properties, which agents are present for example in the senna plants Cassia angustifolia and Cassia acutifolia, from the parts whereof, such as from leaves and pods, they may be isolated by extraction in the form of a raw mixture. The most important of the sennosides are the sennosides A and B of the formula

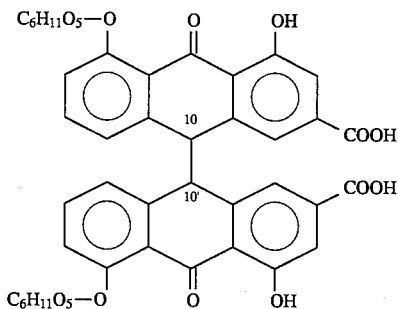

The sennosides A and B are stereoisomers and differ from each other as to the configuration at positions 10 and 10'. Their reduction products are for example rheinanthrone-8-glucoside of the formula

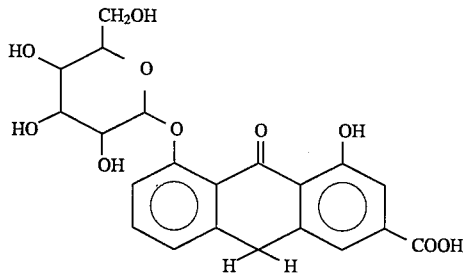

and rhein-8-glucoside (A. Stolle et al., Fortschritte der Chemie organischer Naturstoffe, band 599, 1950, p. 248–269).

The sennoside raw mixture contains, in addition to the desired sennosides, also by-products, for example sennidins (corresponding aglycones), as well as sennoside degradation products, which by-products may give rise to undesired side-effects. The total amount of sennoside type compounds in the raw mixture is approximately 68%, the remaining part being other agents of plant origin.

From the patent and other literature a number of methods and method variants for the recovery of sennosides from senna plants are known. Thus, for example, various extraction methods and combined extraction-crystallization methods for the recovery of sennosides are known, see for example FI-patent 75992 and the literature reference listed therein.

It is also known (i.a. WO 93/00350) to extract senna pods and leaves with a methanol-water-mixture at room temperature and evaporate the methanol to prepare a sennoside raw mixture. In addition, the obtained concentrate can be washed, if desired, for example with an alcohol, such as 2-butanol. Thereafter the sennoside raw mixture obtained can be reduced to form rheinanthrone-8-glucosides. Various reduction reagents, such as stannous(II)chloride, sulphur dioxide, alkalimetal borohydride, and especially alkalimetal dithionite have been suggested for use as reduction agents.

In order to recover the sennosides it is known to oxidize rheinanthrone-8-glucoside back to form the corresponding sennoside compounds. As suitable reagents, i.a. hydrogen peroxide and manganese dioxide have been suggested, but also oxygen, such as atmospheric oxygen. It has also been suggested to facilitate the oxidation by adding a catalyst, palladium black or iron(III) salts having been suggested for this purpose.

SUMMARY OF THE INVENTION

The object of the present invention is an improvement to the afore mentioned known method, which makes it possible to prepare the sennosides A and B with improved yields and purity. The objects of the invention are reached by performing the oxidation of rheinanthrone-8-glucoside using active carbon as the catalyst, and, if desired, the obtained sennosides A and B are converted to their calcium salts by precipitation with methanol from an aqueous solution containing calcium ions.

DETAILED DESCRIPTION OF EXEMPLARY EMBODIMENTS OF THE INVENTION

According to a preferred embodiment of the invention a suitable starting material is provided, such as the pods and leaves of the senna plant, and a sennoside raw mixture is prepared from these by extraction with aqueous methanol, such as with a 45 to 70%, such as with a 50% methanol solution at room temperature, suitably at 20° to 30° C. An exemplary ratio of extraction solution to starting mixture is about 1:1 to 2:1. Thereafter the methanol is removed by evaporation, especially in vacuum and at a temperature of less than 40° C., whereby an aqueous phase containing the sennoside mixture remains. According to a preferred embodiment, the aqueous phase can be washed with a solvent which is only partly soluble in water, for example an alcohol, such as 2-butanol. After washing the layers are allowed to separate and the organic layer, which contains a major part of the by-products of the original sennoside mixture, can be reused for the same purpose after purification, for example distillation. The aqueous phase obtained after washing contains the desired sennosides.

The sennosides may be isolated before reduction by adding an acid, for example strong sulphuric acid, until the pH reaches a value below the pKa-value of the sennosides, that is below appr. 4.

Thereafter the sennoside mixture is subjected to reduction in an aqueous solution. For example alkalimetal dithionite, especially sodium dithionite is used for the reduction. The pH of the reduction is adjusted with an alkalimetal hydroxide, especially sodium hydroxide, to a value of 7 to 10, suitably 8.3. The amount of reduction agent used is to its mass appr. 0.5 to 2 times as compared to the amount of sennosides contained in the solution. The temperature is suitably kept at a value of 15° to 30° C. The reduction normally lasts for appr. 2 to 4 hours.

After the reduction, the rheinanthrone-8-glucoside is precipitated by adding an acid, such as sulphuric acid to a pH of 4 to 5, suitably 4.7, at which pH seed crystals are added and acid is added slowly until the pH is 2 to 3, suitably 2.9. The mixture is cooled to 10° C. and is allowed to crystallize for 1 to 3 hours. The precipitate is filtered under a nitrogen cover, for example by centrifuging. For longer storage, the precipitate can, if needed, be dried also in a heating cabinet.

The obtained rheinanthrone-8-glucoside is thereafter subjected to oxidation by slurrying the same in an alcohol-water mixture, suitably in a 80% isopropanol solution, of which there is suitably for example 10 times compared to the used amount of rheinanthrone-8-glucoside, at a temperature of 0° to 15° C., suitably 5° to 10° C., and by adjusting the pH to 7 to 9 by adding a suitable base, such as alkalimetal hydroxides or alkylamides, suitably triethylamide or diethylamide. During the addition, the pH may not rise above 8.5, because in that case there is the risk that the sugar molecule splits off from the sennoside during the oxidation, whereby the pH rises with 0.5 to 1 units. According to the invention active carbon is then added, suitably OH− -active carbon, in an amount of 0.05 to 0.20 calculated from the amount of rheinanthrone-8-glucoside, suitable at an amount of 0.1 times the said amount. According to the invention, the carbon acts as surface active catalyst, whereby the oxygen adsorbed to the surface of the carbon oxidizes the rheinanthrone-8-glucoside to sennoside A and B much more selectively and effectively than a mere bubbling with air or oxygen. At the same time the active carbon adsorbs unwanted over-oxidized products possibly formed in the reaction, such as rhein-8-glucoside and rhein. Thereafter oxygen or an oxygen source is introduced in the mixture, such as by bubbling air through a sinter, at the above mentioned temperature.

According to the invention it has been discovered that by using especially active carbon as a catalyst instead of the previously suggested catalysts, for example palladium black, or plainly oxygen dissolved in water, good yields and pure products are obtained. The advantages of the efficient catalyst are reflected especially in the sennoside content of the end product, which is over 30% higher compared to a product obtained with a method wherein the oxidation is carried out by dissolving rheinanthrone-8-glucoside in water with calcium hydroxide and by bubbling air through the reaction mixture without active carbon.

The advancement of the reaction can be followed using HPLC whereby the correct finishing point is easily determined by monitoring the concentration of the starting material. The mixture is filtered and the filtrate adjusted with a suitable acid to a pH of 1 to 4, suitably appr. 2, whereby the sennosides A and B, after standing, precipitate in acid form at room temperature. The precipitate obtained can be washed, for example, with isopropanol and dried, for example in a vacuum chamber, however, at the most at a temperature of 40° C., in order to prevent degradation.

According to the invention the sennoside A and B acids obtained can be converted to their calcium salts which are more easily absorbed from the gastrointestinal tract. For this purpose the sennosides are dissolved by raising the pH-value, suitably by adding calcium hydroxide. Calcium hydroxide is added in such an amount that the pH rises to a value of 8.0±0.5, although the sennosides start to dissolve already at a pH of about 5. Alternatively, calcium chloride may added in a molar excess of about 1.1 to 2 as well as sodium hydroxide to the said pH-value. Thereafter the pH is adjusted to appr. 6.7 to 6.9 by adding dilute acid, such as dilute hydrochloric acid in the course of about one hour. The pH can also be adjusted to a value of 6.7 to 8.5, if an endproduct with a higher pH is desired. The pH may not fall below 6.7, because in this case the sennosides start to precipitate as acids from the aqueous solution.

In order to precipitate the calcium salts, methanol is added to the mixture, preferably first an aqueous, such as a 50 to 90%, for example a 90% methanol solution in the course of 15 min to 2 hours, suitably within 1/2 hour, and thereafter pure methanol in the course of 1 to 4, suitably about 2 hours, the mixture is stirred and filtered. The precipitate is dried at a temperature of not more than 40° C., in order to prevent the sennosides from degrading.

The following examples illustrate the invention without limiting the same in any way.

EXAMPLE 1

A. Extraction, evaporation and washing 16 kg of senna pods are digested for 3 days in a mixture of 10 liters of methanol and 10 liters of tap water. The solution is circulated with a pump in order to make the extraction more effective. The temperature is maintained at 20° to 30° C. After the specified time the solution is drained, and the pods washed with 4 l of a 50% methanol solution. The obtained methanol-water-solution is distilled under vacuum at 40° C. The distillation is stopped when the density of the distillation residue is 1.25 kg/l. The distillation residue is extracted with 8 l of n-butanol. The extraction is carrried out in a suitable reaction vessel by mixing the solution for 1.5 hours. The stirring is discontinued and the layers are left to separate over the night. After separation, the aqueous phase is poured into the reduction vessel.

B. Reduction

To the raw aqueous sennoside solution in the reduction vessel at a temperature of 25° C. a 50% sodium hydroxide solution is added until the pH is 8.3. 120 to 150 g of lye is consumed. To the solution 500 g of sodium dithionite is added and the mixture is stirred for two hours. 3 l of water is added, whereafter the pH is adjusted with sulphuric acid to a value of 4.7. 1 g of rheinanthrone-8-glucoside crystals are added and adjusted with sulphuric acid to a pH of 2.9. The mixture is cooled to 10° C., where it is kept for two hours. The crystallized rheinanthrone-8-glucoside is filtered onto a filter and washed with 1500 ml of hot water. The precipitate is dried by sucking nitrogen through the filter under vacuum, whereby appr. 560 g of rheinanthrone-8-glucoside is obtained, which contains about 20% moisture.

C. Oxidation of rheinanthrone-8-glucoside 560 g of rheinanthrone-8-glucoside containing 15–20% moisture is slurried in 6000 ml of 80% (vol./vol.)isopropanol at +5° to +10° C. The rheinanthrone-8glucoside is made to dissolve by adding triethylamine to a pH of appr. 8. The pH may not rise above 8.5. Appr. 200 ml of triethylamine is consumed. Thereafter 50 g of OH− active carbon is added and the introduction of pressurized air into the mixture is started by bubbling through a sinter at a rate of appr. 3 liters in a minute. Air is bubbled for appr. 2 1/2hours, the temperature of the reaction mixture being 5° to 10° C.

When the reaction is complete, the mixture is filtered through filter cardboard and adjusted with concentrated hydrochloric acid (about 200 ml) to a pH-value of 1.5 to 2.0. The mixture is left to crystallize over night at room temperature while stirring. The obtained precipitate is filtered through cardboard, washed with 500 ml of isopropanol and dried in a vacuum chamber at a temperature of not more than appr. 40° C. The yield is appr. 310 g (appr. 62.2% calculated from the rheinanthrone-8-glucoside).

D. Preparation of the calcium salt 300 g of sennoside A + B acid is slurried in 1800 ml of water and dissolved by adding a calcium hydroxide-water slurry (30 g Ca(OH)$_2$ +150 ml of water). The addition is continued to a pH value of 8±0.5 and appr. 110 ml of lime slurry is consumed to dissolve the acid. Thereafter the pH is adjusted with weak hydrochloric acid (40 ml; 1:10 dilution) to a pH-value of 6.7 in the course of one hour, while making sure that the pH stays in the range of 6.7 to 6.9. Within ½ hour 1000 ml of a 90% methanol solution and thereafter, during appr. 2 hours, 4400 ml pure (100%) methanol are added. The mixture is stirred for another hour and filtered through cardboard. The precipitate is washed with a small amount of methanol.

The precipitate is dried at a temperature of at the most 40° C. over night and weighed. The yield is appr. 317 g (100%) as air-dry and 285 g (appr. 91%) as vacuum dry calculated from the sennoside A + B acid, of which the sennoside content is appr. 82%.

I claim:

1. A process for the preparation of sennosides A and B, wherein rhein-9-anthrone-8-glucoside is oxidized with oxygen or an oxygen source to the sennosides A and B, wherein the oxidation is carried out using active carbon as a catalyst.

2. The process according to the claim 1, wherein the oxidation is carried out in an aqueous solution and at an alkaline pH-value.

3. The process according to claim 1 or 2, wherein an oxygen containing gas is used for the oxidation.

4. The process according to claim 1, characterized in that the rheinanthrone-8-glucoside is made by reducing a sennoside mixture obtained by extracting senna plants or parts thereof.

5. The process according to claim 4, characterized in that the reduction is carried out in an aqueous solution using alkalimetal dithionite.

6. The process according to claim 4 or 5, characterized in that the extraction is carried out using a water-methanol-mixture, by evaporating the methanol, and washing the aqueous phase with an alcohol.

7. The process according to claim 1, characterized in that after the oxidation, the sennosides A and B are recovered by crystallization by acidifying the reaction mixture to a pH-value of 1.5 to 2.0.

8. The process according to claim 1, characterized in that the sennosides A and B are converted to their calcium salts by dissolving the sennosides in an aqueous solution by adding calcium hydroxide, and precipitating them as calcium salts by adding methanol.

9. The process according to claim 8, characterized in that for the precipitation, the pH is adjusted to a value of 6.7 to 6.9.

* * * * *